United States Patent
Hsieh et al.

(10) Patent No.: US 7,320,776 B2
(45) Date of Patent: Jan. 22, 2008

(54) FLUID ANALYTICAL DEVICES

(75) Inventors: Wen-Pin Hsieh, Sanwan Township, Miaoli County (TW); Chin-Tang Chuang, Pingjhen (TW); Jian-Je Jian, Sijhih (TW); Iany-H Liau, Taipei (TW); Ke-Shieng Yang, Taipei (TW)

(73) Assignees: Industrial Technology Research Institute, Hsinchu (TW); Apex Biotechnology Corp., Hsinchu (TW)

( * ) Notice: Subject to any disclaimer, the term of this patent is extended or adjusted under 35 U.S.C. 154(b) by 0 days.

(21) Appl. No.: 11/175,131

(22) Filed: Jul. 5, 2005

(65) Prior Publication Data

US 2006/0133958 A1 Jun. 22, 2006

(30) Foreign Application Priority Data

Dec. 22, 2004 (TW) .............................. 93140063 A

(51) Int. Cl.
*G01N 9/30* (2006.01)
*G01N 35/00* (2006.01)
*B01L 11/00* (2006.01)
*B01D 21/26* (2006.01)

(52) U.S. Cl. .......................... 422/72; 422/101; 436/45; 210/787

(58) Field of Classification Search .................. 436/45
See application file for complete search history.

(56) References Cited

U.S. PATENT DOCUMENTS

| | | | | |
|---|---|---|---|---|
| 5,061,381 A | | 10/1991 | Burd ........................... 210/789 |
| 5,077,013 A | * | 12/1991 | Guigan ........................ 422/64 |
| 5,089,417 A | * | 2/1992 | Wogoman ..................... 436/45 |
| 5,160,702 A | * | 11/1992 | Kopf-Sill et al. ............. 422/72 |
| 5,242,803 A | * | 9/1993 | Burtis et al. ................ 435/7.92 |
| 5,498,392 A | * | 3/1996 | Wilding et al. ............ 422/68.1 |
| 5,842,787 A | * | 12/1998 | Kopf-Sill et al. ........... 366/340 |
| 5,916,522 A | | 6/1999 | Boyd et al. .................... 422/58 |
| 5,919,711 A | | 7/1999 | Boyd et al. ................. 436/178 |
| 6,002,475 A | | 12/1999 | Boyd et al. ................. 356/246 |
| 6,033,914 A | | 3/2000 | Boyd et al. ................. 436/178 |
| D424,956 S | | 5/2000 | von Buelow et al. ........ D10/81 |
| 6,326,211 B1 | * | 12/2001 | Anderson et al. ........... 436/177 |
| 6,348,176 B1 | | 2/2002 | Hammer et al. .............. 422/64 |
| 6,391,264 B2 | | 5/2002 | Hammer et al. .............. 422/72 |
| 6,531,095 B2 | | 3/2003 | Hammer et al. .............. 422/64 |

* cited by examiner

*Primary Examiner*—Jill Warden
*Assistant Examiner*—Neil Turk
(74) *Attorney, Agent, or Firm*—Thomas, Kayden, Horstemeyer & Risley

(57) ABSTRACT

A fluid analytical device for separating and analyzing a fluid including a first component and a second component. The specific weight of the first component exceeds that of the second component. A rotating base includes a receiving chamber, a first separation well, a second separation well, a first connection channel, a second connection channel, and a vent channel. The receiving chamber receives the fluid. The first connection channel connects the receiving chamber to the first separation well. The second connection channel connects the first separation well to the second separation well. The vent channel is connected to the receiving chamber. The distance from the first separation well to the receiving chamber exceeds that from the second separation well to the receiving chamber. When the rotating base rotates, the first and second components of the fluid flow into the first and second separation wells by centrifugal force, respectively.

12 Claims, 4 Drawing Sheets

FLUID ANALYTICAL DEVICES

BACKGROUND

The invention relates to fluid analytical devices, and in particular to fluid analytical devices providing multi-step analysis and detection functions.

Generally, when blood detection is performed, blood cells and plasma must be separated from whole blood, thereafter detection can be performed on the plasma. Conventionally, plasma is separated from whole blood by centrifugal force using a centrifugal rotor with specific channels.

U.S. Pat. No. 5,061,381 discloses a centrifugal rotor capable of separating cellular components and plasma from whole blood. As shown in FIG. 1, the centrifugal rotor 10 comprises a top layer 12, a middle layer 14, and a bottom layer 16. The top layer 12, middle layer 14, and bottom layer 16 respectively provide different channels. Whole blood can be input to the centrifugal rotor 10 via a blood application port 22. The cellular components and plasma can be separated from the whole blood by rotation of the centrifugal rotor 10 and interaction of the top layer 12, middle layer 14, and bottom layer 16. Specifically, as having different specific weights, the cellular components and plasma move radially and are separated by centrifugal force generated during rotation of the centrifugal rotor 10.

Nevertheless, the aforementioned centrifugal rotor 10 has the following drawbacks. As shown in FIG. 2, the simultaneously and radially moving cellular components and plasma separate at radial passages 94. The cellular components are stopped by the narrow radial passages 94 and remain at a peripheral wall 91 of a collection chamber 90, while the plasma continues to flow into test wells 92 via the radial passages 94. Although most cellular components are stopped by the narrow radial passages 94 and cannot flow into the test wells 92 during operation of the centrifugal rotor 10, some cellular components may, however, be pushed into the radial passages 94 by centrifugal force. At this point, the cellular components (blood cells) are subject to compression of the radial passages 94 and shear force. The cellular components (blood cells) are thus broken and flow into the test wells 92, contaminating the plasma therein and adversely affecting subsequent analysis of the plasma.

Moreover, to prevent overflow of whole blood during rotation of the centrifugal rotor 10, an overflow chamber 44 is disposed in the middle layer 14 to collect the overflowing whole blood.

In its entirety, as shown in FIG. 1 and FIG. 2, the structure (or channel structure) of the centrifugal rotor 10 is complex, and potentially inconvenient to manufacture or operate.

Hence, there is a need for a fluid analytical device providing a simplified structure and easy operation. The fluid analytical device can provide the functions of multi-step fluid analysis and detection.

SUMMARY

Accordingly, an exemplary embodiment of the invention provides a fluid analytical device for separating and analyzing a fluid comprising a first component and a second component. The specific weight of the first component exceeds that of the second component. The fluid analytical device comprises a rotating base comprising a receiving chamber, a first separation well, a second separation well, a first connection channel, a second connection channel, and a vent channel. The receiving chamber receives the fluid. The first connection channel connects the receiving chamber to the first separation well. The second connection channel connects the first separation well to the second separation well. The vent channel is connected to the receiving chamber. The distance from the first separation well to the receiving chamber exceeds that from the second separation well to the receiving chamber. When the rotating base rotates, the first component of the fluid flows into the first separation well via the first connection channel by centrifugal force and friction while the second component flows into the second separation well via the first connection channel, first separation well, and second connection channel by the difference of componential vectors of the centrifugal force and the specific weight of the second component less than that of the first component.

In an embodiment of the fluid analytical device, the rotating base further comprises an input hole connected to the receiving chamber. The fluid is input to the receiving chamber via the input hole.

In an embodiment of the fluid analytical device, the vent channel is connected between the second separation well and the receiving chamber. Gas in the first connection channel, first separation well, second connection channel, and second separation well is discharged via the vent channel, receiving chamber, and input hole when the rotating base rotates.

In an embodiment of the fluid analytical device, the distance from the first separation well to the receiving chamber exceeds that from the second separation well to the receiving chamber.

In an embodiment of the fluid analytical device, a first included angle between the first and second connection channels is between 0° and 90°.

In an embodiment of the fluid analytical device, the proportion of the cross-sectional area of the first connection channel to that of the second connection channel exceeds or equals 1.

In an embodiment of the fluid analytical device, the cross-sectional area of the vent channel is less than 1 $mm^2$.

In an embodiment of the fluid analytical device, the fluid further comprises a third component, and the rotating base further comprises a third separation well and a third connection channel. The specific weight of the second component exceeds that of the third component. The third connection channel connects the second separation well to the third separation well. The distance from the second separation well to the receiving chamber exceeds that from the third separation well to the receiving chamber. When the rotating base rotates, the third component flows into the third separation well via the first connection channel, first separation well, second connection channel, second separation well, and third connection channel by the centrifugal force.

In an embodiment of the fluid analytical device, the vent channel is connected between the third separation well and the receiving chamber. Gas in the first connection channel, first separation well, second connection channel, second separation well, third connection channel, and third separation well is discharged via the vent channel, receiving chamber, and input hole when the rotating base rotates.

In an embodiment of the fluid analytical device, the proportion of the distance between the first separation well and the receiving chamber to that between the second separation well and the receiving chamber is between 1 and 8, and the proportion of the distance between the first separation well and the receiving chamber to that between the third separation well and the receiving chamber is between 1 and 10.

In an embodiment of the fluid analytical device, a first included angle between the first and second connection channels is between 0° and 90°, and a second included angle between the second and third connection channels is less than 180°.

In an embodiment of the fluid analytical device, the proportion of the cross-sectional area of the first connection channel to that of the second connection channel is between 1 and 5, and the proportion of the 5, cross-sectional area of the first connection channel to that of the third connection channel is between 1 and 8.

In an embodiment of the fluid analytical device, the receiving chamber is disposed on the center of the rotating base.

DESCRIPTION OF THE DRAWINGS

The invention can be more fully understood by reading the subsequent detailed description and examples with references made to the accompanying drawings, wherein.

DETAILED DESCRIPTION

First Embodiment

Figure 1:
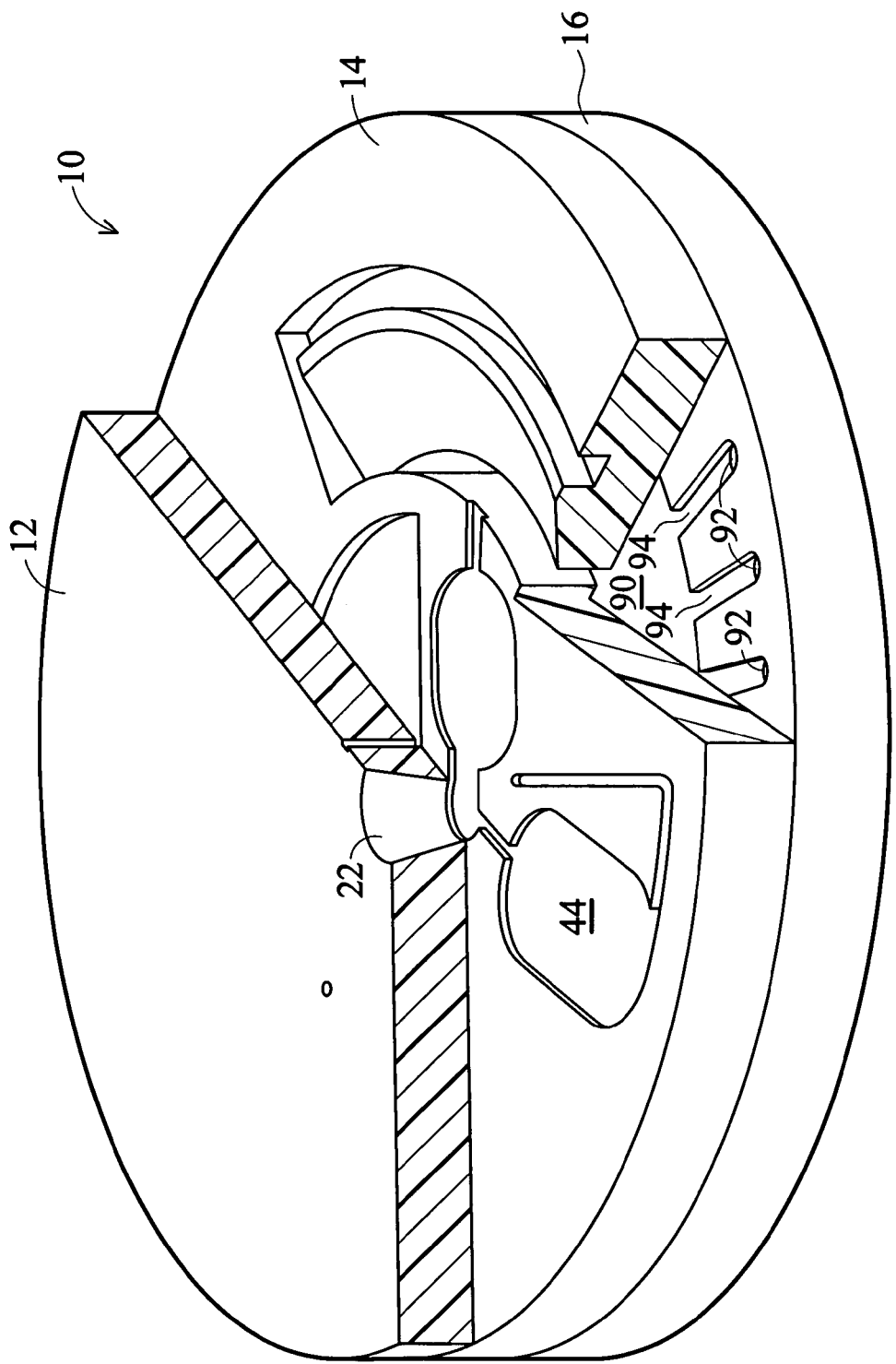
FIG. 1 is a perspective view of a conventional centrifugal rotor, with portions broken away.
Figure 2:
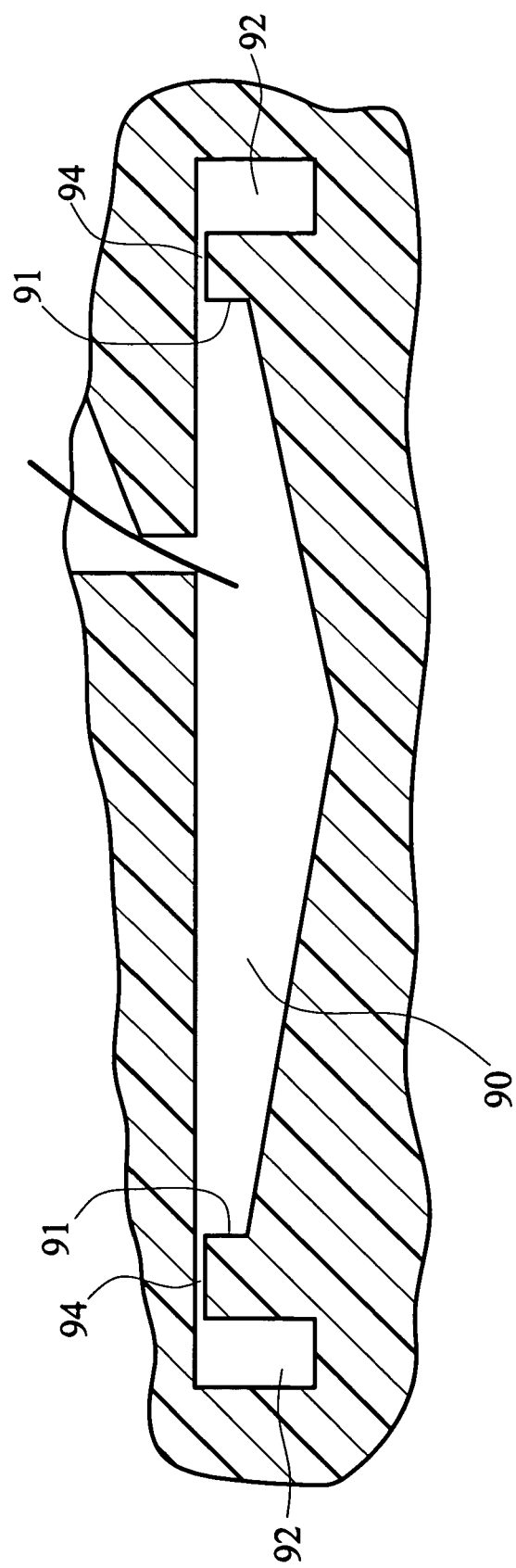
FIG. 2 is a partial cross section of FIG. 1.
Figure 3:
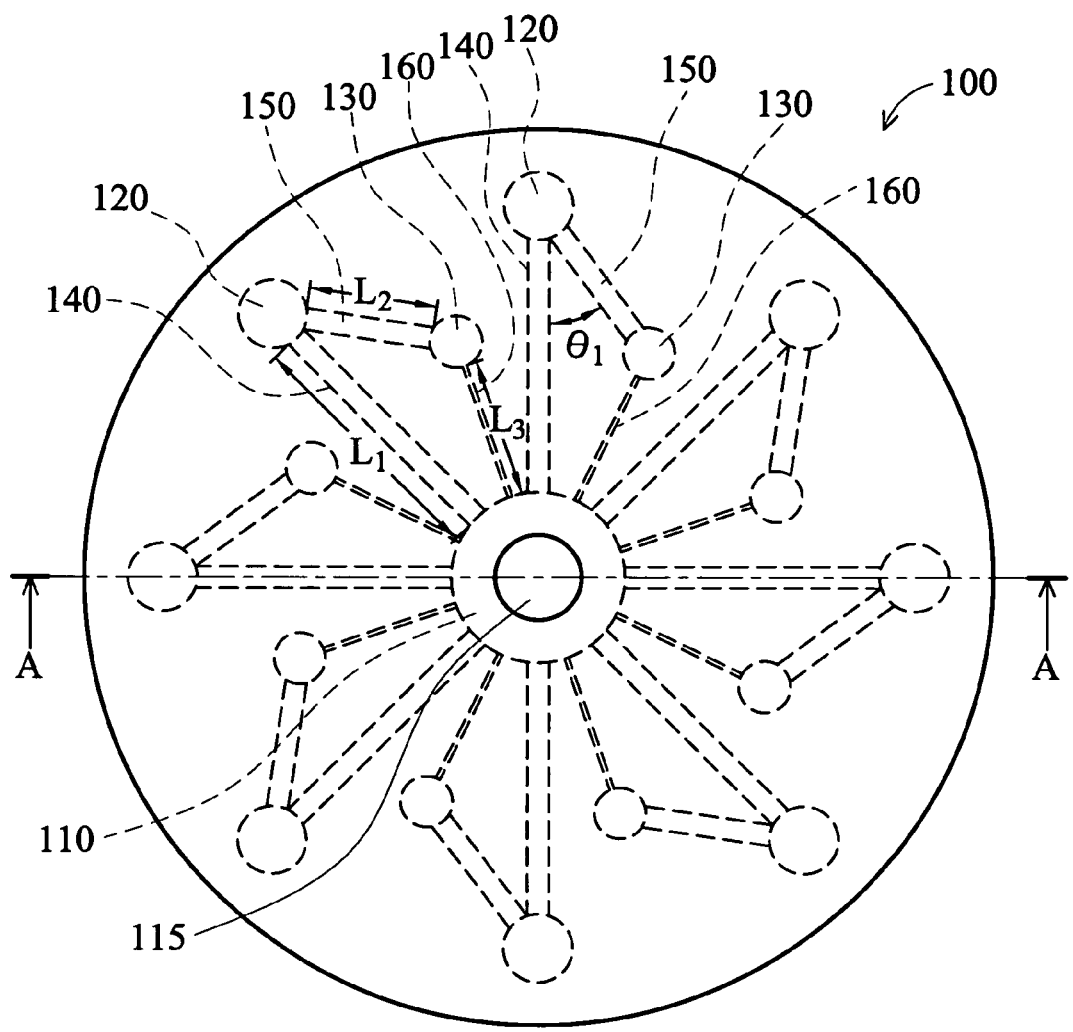
FIG. 3 is a schematic top view of the fluid analytical device of a first embodiment of the invention.
Figure 4:
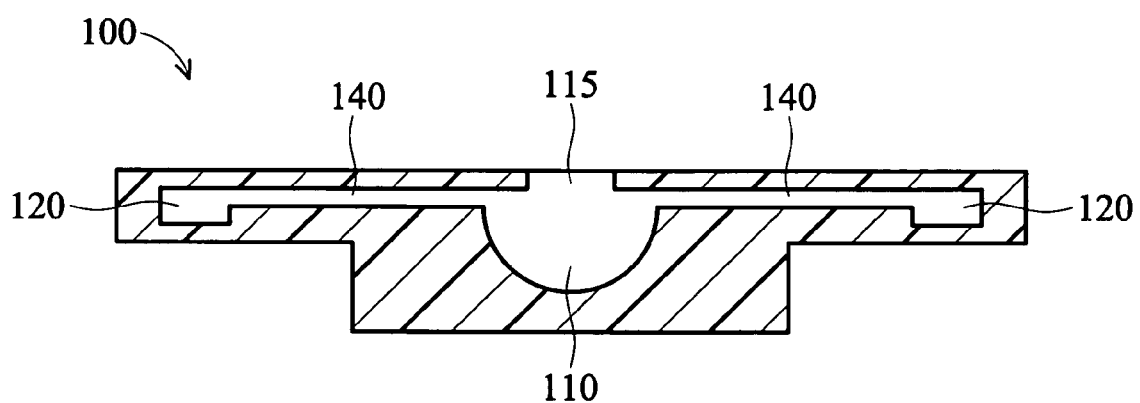
FIG. 4 is a schematic cross section taken along A-A of FIG. 3.

Referring to FIG. 3 and FIG. 4, the fluid analytical device comprises a rotating base 100 comprising a receiving chamber 110, an input hole 115, a plurality of first separation wells 120, a plurality of second separation wells 130, a plurality of first connection channels 140, a plurality of second connection channels 150, and a plurality of vent channels 160. Each first separation well 120, each second separation well 130, each first connection channel 140, each second connection channel 150, each vent channel 160, and receiving chamber 110 construct a circulation group. The rotating base 100 of this embodiment may comprise, for example, eight circulation groups.

The receiving chamber 110 is disposed on the center of the rotating base 100. The input hole 115 is disposed on the rotating base 100 and is connected to the receiving chamber 110. The first connection channels 140 connect the receiving chamber 110 to the first separation wells 120. The second connection channels 150 connect the first separation wells 120 to the second separation wells 130. The vent channels 160 are connected between the second separation wells 130 and the receiving chamber 110.

As shown in FIG. 3, in each circulation group, the distance L1 (the length of the first connection channel 140) which is the minimum distance between the edge of the first separation well 120 and the edge of the receiving chamber 110 exceeds the distance L3 (the length of the vent channel 160) which is the minimum distance between the edge of the second separation well 130 and the edge of the receiving chamber 110. Specifically, the proportion of the length $L_1$ of the first connection channel 140 to the length $L_2$ of the second connection channel 150 exceeds 1, or a first included angle $\theta_1$ between the first connection channel 140 and the second connection channel 150 is between 0° and 90°.

Additionally, the proportion of the cross-sectional area of the first connection channel 140 to that of the second connection channel 150 exceeds or equals 1, and the cross-sectional area of the vent channel 160 may be less than 1 mm². Specifically, the cross-sectional area of the vent channel 160 must be very small, such that a fluid cannot easily enter.

The following description is directed to operation of the fluid analytical device of this embodiment, by which a fluid is separated and analyzed.

Various (powdery) detection reagents are immobilized in the first separation wells 120 and second separation wells 130. A fluid (such as whole blood) is input to the receiving chamber 110 via the input hole 115. The fluid (whole blood) may be composed of a first component (such as blood cells or cells) and a second component (such as plasma), in which the specific weight of the first component (blood cells or cells) exceeds that of the second component (plasma). The bottom of the rotating base 100 can be connected to a motor (not shown), and the rotating base 100 rotates at a specific rotational speed. At this point, the fluid (whole blood) in the receiving chamber 110 rotates with the rotating base 100 due to friction between the fluid (whole blood) and the inner wall of the receiving chamber 110 and rises along the inner wall of the receiving chamber 110. When rising to the entrance of each first connection channel 140, the fluid (whole blood) flows toward the first separation wells 120 by centrifugal force and capillarity. Specifically, the first component (blood cells or cells) with the greater specific weight stops in the first separation wells 120, while the second component (plasma) with the smaller specific weight gradually flows into the second separation wells 130 via the second connection channels 150 by the difference of componential vectors of the centrifugal force. Additionally, when the rotating base 100 rotates, gas in the first connection channels 140, first separation wells 120, second connection channels 150, and second separation wells 130 is discharged via the vent channels 160, receiving chamber 110, and input hole 115, thereby balancing the pressure difference among the circulation groups. The detection reagents immobilized in the first separation wells 120 and second separation wells 130 then react with the first component (blood cells or cells) and second component (plasma), respectively. Accordingly, analysis of the fluid (whole blood) can be obtained by observing results of reactions in the first separation wells 120 and second separation wells 130.

Moreover, the aforementioned fluid is not limited to whole blood. Namely, the fluid may be a solution including metabolic products of organisms, a solid-liquid mixed solution, and so on.

Moreover, the fluid may be a pure solvent and can be continuously analyzed by the fluid analytical device of this embodiment. Similarly, various (powdery) detection reagents are immobilized in the first separation wells 120 and second separation wells 130. The fluid (pure solvent) is input to the receiving chamber 110 via the input hole 115. The rotating base 100 then rotates at a specific rotational speed. At this point, the fluid (pure solvent) flows toward the first separation wells 120 by centrifugal force and capillarity. The fluid (pure solvent) further flows into the second separation wells 130 until balance of the pressure difference among the circulation groups is achieved. The detection reagents immobilized in the first separation wells 120 and second separation wells 130 then react with the fluid (pure solvent), respectively. Accordingly, analysis of the fluid (pure solvent) can be obtained by observing results of reactions in the first separation wells 120 and second separation wells 130.

Moreover, although utilizing eight circulation groups to separate and analyze a fluid, the fluid analytical device of this embodiment is not limited to having only eight circulation groups. Namely, the fluid analytical device may have more than eight circulation groups to separate and analyze a fluid. Furthermore, each circulation group of this embodiment is not limited to having only two separation wells. Namely, each circulation group may have more than two separation wells as required, enabling multiple separation and analysis of a fluid.

Second Embodiment

Elements corresponding to those of the first embodiment share the same reference numerals.

Figure 5:
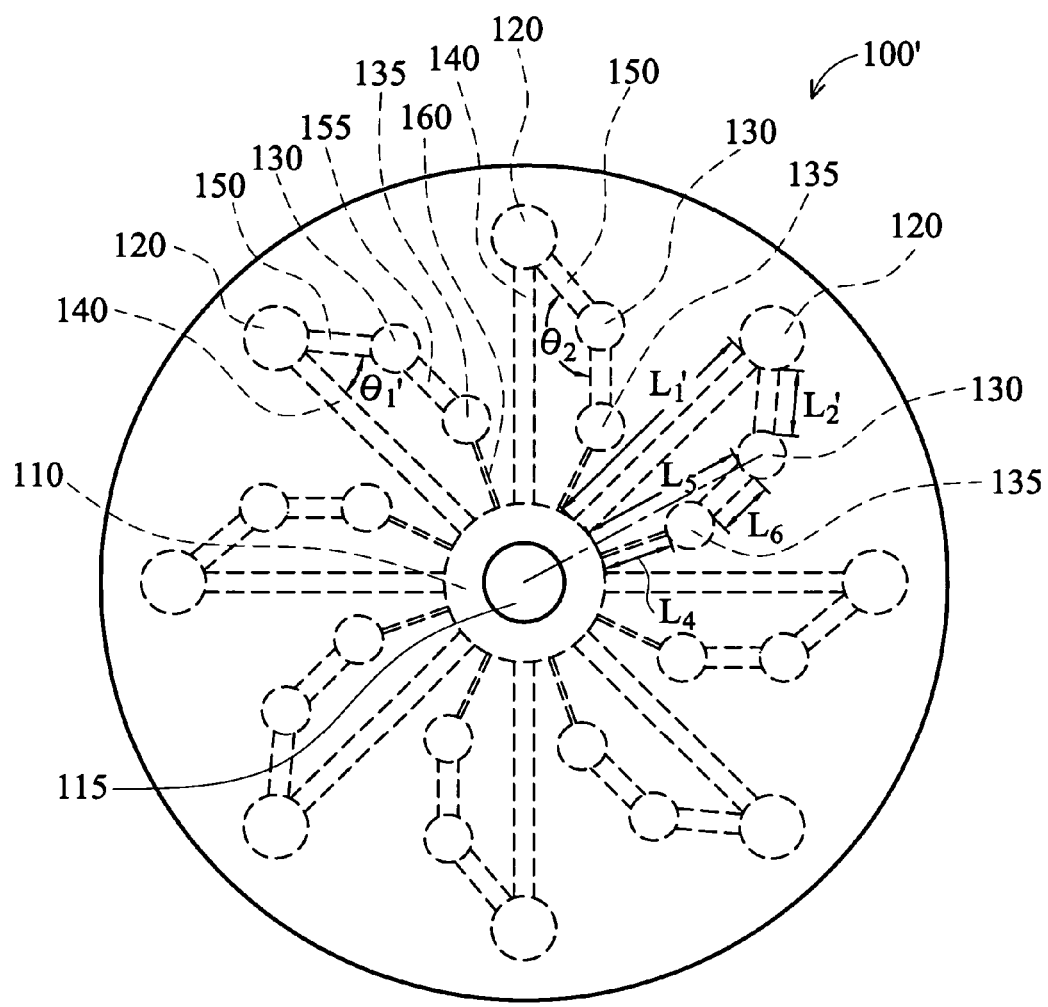
FIG. 5 is a schematic top view of the fluid analytical device of a second embodiment of the invention.

Referring to FIG. 5, the fluid analytical device comprises a rotating base 100' comprising a receiving chamber 110, an input hole 115, a plurality of first separation wells 120, a plurality of second separation wells 130, a plurality of third separation wells 135, a plurality of first connection channels 140, a plurality of second connection channels 150, a plurality of third connection channels 155, and a plurality of vent channels 160. Each first separation well 120, each second separation well 130, each third separation well 135, each first connection channel 140, each second connection channel 150, each third connection channel 155, each vent channel 160, and the receiving chamber 110 construct a circulation group. The rotating base 100' of this embodiment may comprise, for example, eight circulation groups.

The receiving chamber 110 is disposed on the center of the rotating base 100'. The input hole 115 is disposed on the rotating base 100' and is connected to the receiving chamber 110. The first connection channels 140 connect the receiving chamber 110 to the first separation wells 120. The second connection channels 150 connect the first separation wells 120 to the second separation wells 130. The third connection channels 155 connect the second separation wells 130 to the third separation wells 135. The vent channels 160 are connected between the third separation wells 135 and the receiving chamber 110.

As shown in FIG. 5, in each circulation group, the distance L1' (the length of the first connection channel 140) which is the minimum distance between the edge of the first separation well 120 and the edge of the receiving chamber 110 exceeds the distance L5 which is the minimum distance between the edge of the second separation well 130 and the edge of the receiving chamber 110. The distance L5 exceeds the distance L4 (the length of the vent channel 160) which is the minimum distance between the edge of the third separation well 135 and the edge of the receiving chamber 110. Specifically, the proportion of the distance L1' to the distance L5 is between 1 and 8, and the proportion of the distance $L_1'$ to the distance $L_4$ is between 1 and 10. Additionally, a first included angle $\theta_1'$ between the first connection channel 140 and the second connection channel 150 is between 0° and 90°, and a second included angle $\theta_2$ between the second connection channel 150 and the third connection channel 155 is less than 180°.

Additionally, the proportion of the cross-sectional area of the first connection channel 140 to that of the second connection channel 150 is between 1 and 5, the proportion of the cross-sectional area of the first connection channel 140 to that of the third connection channel 155 is between 1 and 8, and the cross-sectional area of the vent channel 160 may be less than 1 mm². Similarly, the cross-sectional area of the vent channel 160 must be very small, such that a fluid cannot easily enter.

The following description is directed to operation of the fluid analytical device of this embodiment, by which a fluid is separated and analyzed.

Various (powdery) detection reagents are immobilized in the first separation wells 120, second separation wells 130, and third separation wells 135. A fluid (such as a multiple-phase mixed solution) is input to the receiving chamber 110 via the input hole 115. The fluid may be composed of a first component, a second component, and a third component, in which the specific weight of the first component exceeds that of the second component and the specific weight of the second component exceeds that of the third component. The bottom of the rotating base 100' can be connected to a motor (not shown), and the rotating base 100' rotates at a specific rotational speed. At this point, the fluid in the receiving chamber 110 rotates with the rotating base 100' due to friction between the fluid and the inner wall of the receiving chamber 110 and rises along the inner wall of the receiving chamber 110. When rising to the entrance of each first connection channel 140, the fluid flows toward the first separation wells 120 by centrifugal force and capillarity. Specifically, the first component with the greatest specific weight stops in the first separation wells 120, while the second and third components with the smaller specific weights gradually flow into the second separation wells 130 via the second connection channels 150 by the difference of componential vectors of the centrifugal force. The second component then stops in the second separation wells 130, while the third component with the smallest specific weight gradually flows into the third separation wells 135 via the third connection channels 155 by the difference of componential vectors of the centrifugal force. Additionally, when the rotating base 100' rotates, gas in the first connection channels 140, first separation wells 120, second connection channels 150, second separation wells 130, third connection channels 155, and third separation wells 135 is discharged via the vent channels 160, receiving chamber 110, and input hole 115, thereby balancing the pressure difference among the circulation groups. The detection reagents immobilized in the first separation wells 120, second separation wells 130, and third separation wells 135 then react with the first, second, and third components, respectively. Accordingly, analysis of the fluid can be obtained by observing results of reactions in the first separation wells 120, second separation wells 130, and third separation wells 135.

Similarly, the aforementioned fluid may also be a solution including metabolic products of organisms, a solid-liquid mixed solution, and so on.

Similarly, the fluid may be a pure solvent and can be continuously analyzed by the fluid analytical device of this embodiment. Various (powdery) detection reagents can be immobilized in the first separation wells 120, second separation wells 130, and third separation wells 135. The fluid (pure solvent) is input to the receiving chamber 110 via the input hole 115. The rotating base 100' then rotates at a specific rotational speed. At this point, the fluid (pure solvent) flows toward the first separation wells 120 by centrifugal force and capillarity. The fluid (pure solvent) further flows into the second separation wells 130 and third separation wells 135 until balance of the pressure difference among the circulation groups is achieved. The detection reagents immobilized in the first separation wells 120, second separation wells 130, and third separation wells 135 then react with the fluid (pure solvent), respectively. Accordingly, analysis of the fluid (pure solvent) can be obtained by observing results of reactions in the first separation wells 120, second separation wells 130, and third separation wells 135.

Similarly, although utilizing eight circulation groups to separate and analyze a fluid, the fluid analytical device of this embodiment is not limited to having only eight circulation groups. Namely, the fluid analytical device may have more than eight circulation groups to separate and analyze a fluid. Furthermore, each circulation group of this embodiment is not limited to having only three separation wells. Namely, each circulation group may have more than three separation wells as required, enabling multiple separation and analysis of a fluid.

In conclusion, the disclosed fluid analytical device has many advantages as follows. The structure of the fluid analytical device is simplified. Multi-step or multi-route analysis of a fluid can be performed by the simplified fluid analytical device. Specifically, various detections of a fluid are performed in individual separation wells, thereby not interfering with each other. Moreover, after the separation wells are filled with a fluid, the fluid can no longer flow into the separation wells no matter how the rotational speed of the rotating base alters. Thus, quantitative detection of the fluid can be accomplished, and design of an overflow chamber can be omitted. Furthermore, the fluid can be uniformly distributed in each circulation group of the fluid analytical device and components (with different specific weights) in the fluid can be separated, in the absence of filters or valves.

While the invention has been described by way of example and in terms of preferred embodiment, it is to be understood that the invention is not limited thereto. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A fluid analytical device for separating and analyzing a fluid comprising a first component and a second component, wherein the specific weight of the first component exceeds that of the second component, comprising:
   a rotating base comprising a receiving chamber, a first separation well, a second separation well, a first connection channel, a second connection channel, and a vent channel, wherein the receiving chamber receives the fluid, the first connection channel directly connects the receiving chamber to the first separation well, the second connection channel directly connects the first separation well to the second separation well, the vent channel is directly connected between the second separation well and the receiving chamber, the minimum distance between edges of the first separation well and the receiving chamber exceeds the minimum distance between edges of the second separation well and the receiving chamber,
   whereby, when the rotating base rotates, the first component of the fluid flows into the first separation well via the first connection channel by centrifugal force and friction while the second component flows into the second separation well via the first connection channel, first separation well, and second connection channel by the difference of componential vectors of the centrifugal force and the specific weight of the second component less than that of the first component.

2. The fluid analytical device as claimed in claim 1, wherein the rotating base further comprises an input hole connected to the receiving chamber, and the fluid is input to the receiving chamber via the input hole.

3. The fluid analytical device as claimed in claim 1, wherein a first included angle between the first and second connection channels is between 0° and 90°.

4. The fluid analytical device as claimed in claim 1, wherein the proportion of the cross-sectional area of the first connection channel to that of the second connection channel exceeds or equals 1.

5. The fluid analytical device as claim in claim 1 wherein the cross-sectional area of the vent channel is less than 1 $mm^2$.

6. The fluid analytical device as claimed in claim 1, wherein the fluid further comprises a third component, the rotating base further comprises a third separation well and a third connection channel, the specific weight of the second component exceeds that of the third component, the third connection channel connects the second separation well to the third separation well, the minimum distance between the edges of the second separation well and the receiving chamber exceeds the minimum distance between edges of the third separation well and the receiving chamber, whereby, when the rotating base rotates, the third component flows into the third separation well via the first connection channel, first separation well, second connection channel, second separation well, and third connection channel by the centrifugal force.

7. The fluid analytical device as claimed in claim 6, wherein the rotating base further comprises an input hole connected to the receiving chamber, and the fluid is input to the receiving chamber via the input hole.

8. The fluid analytical device as claimed in claim 6, wherein the proportion of the minimum distance between the edges of the first separation well and the receiving chamber to the minimum distance between the edges of the second separation well and the receiving chamber is between 1 and 8, and the proportion of the minimum distance between the edges of the first separation well and the receiving chamber to the minimum distance between the edges of the third separation well and the receiving chamber is between 1 and 10.

9. The fluid analytical device as claimed in claim 6, wherein a first included angle between the first and second connection channels is between 0° and 90°, a second included angle between the second and third connection channels is less than 180°.

10. The fluid analytical device as claimed in claim 6, wherein the proportion of the cross-sectional area of the first connection channel to that of the second connection channel is between 1 and 5, and the proportion of the cross-sectional area of the first connection channel to that of the third connection channel is between 1 and 8.

11. The fluid analytical device as claim in claim 9, wherein the cross-sectional area of the vent channel is less than 1 $mm^2$.

12. The fluid analytical device as claimed in claim 1, wherein the receiving chamber is disposed on a rotational center of the rotating base.

* * * * *